(12) United States Patent
Rivera et al.

(10) Patent No.: US 8,721,586 B1
(45) Date of Patent: May 13, 2014

(54) INTRODUCER FOR PERCUTANEOUS ENDOSCOPIC GASTROSTOMY APPLIANCE

(71) Applicants: Stephanie Rivera, Burlington, NC (US); Hilbert Brown, Winston-Salem, NC (US); Smitha Raghunathan, Winston-Salem, NC (US); Gregory Bates, Advance, NC (US); Caroline Gayzik, Winston-Salem, NC (US)

(72) Inventors: Stephanie Rivera, Burlington, NC (US); Hilbert Brown, Winston-Salem, NC (US); Smitha Raghunathan, Winston-Salem, NC (US); Gregory Bates, Advance, NC (US); Caroline Gayzik, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/778,951

(22) Filed: Feb. 27, 2013

Related U.S. Application Data

(60) Provisional application No. 61/738,608, filed on Dec. 18, 2012.

(51) Int. Cl.
*A61M 37/00* (2006.01)
*A61M 31/00* (2006.01)
*A61M 25/00* (2006.01)

(52) U.S. Cl.
USPC ........................................ 604/93.01; 604/523

(58) Field of Classification Search
USPC ............ 604/93.01, 103.03, 103.05, 104, 115, 604/164.04–164.1, 174–179, 533–535
See application file for complete search history.

(56) References Cited

U.S. PATENT DOCUMENTS

| 8,057,429 B2 | 11/2011 | Nath | |
| 2004/0111056 A1* | 6/2004 | Weststrate et al. | 604/104 |
| 2006/0052752 A1* | 3/2006 | McMichael | 604/175 |

FOREIGN PATENT DOCUMENTS

WO   WO 2010/075032 A1   7/2010

OTHER PUBLICATIONS

Suzuki, Rei et al., "Prospective randomized comparative study of hemodynamic changes between ultrathin transnasal and conventional transoral esophagogastroduodenoscopy in percutaneous endoscopic gastronomy placement with modified introducer method under sedation," Fukushima Journal of Medicine, vol. 57(1), 2011, pp. 28-32.
Unknown author, "IDEAL," Olympus Endo Therapy, published prior to at least Dec. 18, 2012, 6 pages.
Unknown author, "Direct PEG IDEAL," Olympus Endo Therapy, published prior to at least Dec. 18, 2012, 8 pages.
Unknown author, "Percutaneous Endoscopic Gastronomy Systems—FLOW / PEG Push Technique," Cook Medical, published prior to at least Dec. 18, 2012, 4 pages.
Unknown author, "Percutaneous Endoscopic Gastronomy Systems—FLOW / PEG Pull Technique," Cook Medical, published prior to at least Dec. 18, 2012, 4 pages.

* cited by examiner

*Primary Examiner* — Laura Bouchelle
*Assistant Examiner* — Leah Stohr
(74) *Attorney, Agent, or Firm* — Brinks Gilson & Lione

(57) ABSTRACT

A percutaneous gastrostomy introduction system may include may include an elongate tube assembly including one or both of a dilator portion and a gastrostomy tube portion, which may be continuously formed or joined by one or more connection joints that may—in certain embodiments—provide for rotation about a common longitudinal axis. The dilator portion includes a helical surface for advancing contact with body tissue and may be disposed near (including up to and defining) a first end of the elongate tube assembly. An engagement structure, including—for example—one or more of a wire loop, a user-graspable handle, or another graspable structure may be included at the first end of the device. Device embodiments may be effective to lessen or prevent tenting of patient tissue during introduction.

20 Claims, 4 Drawing Sheets

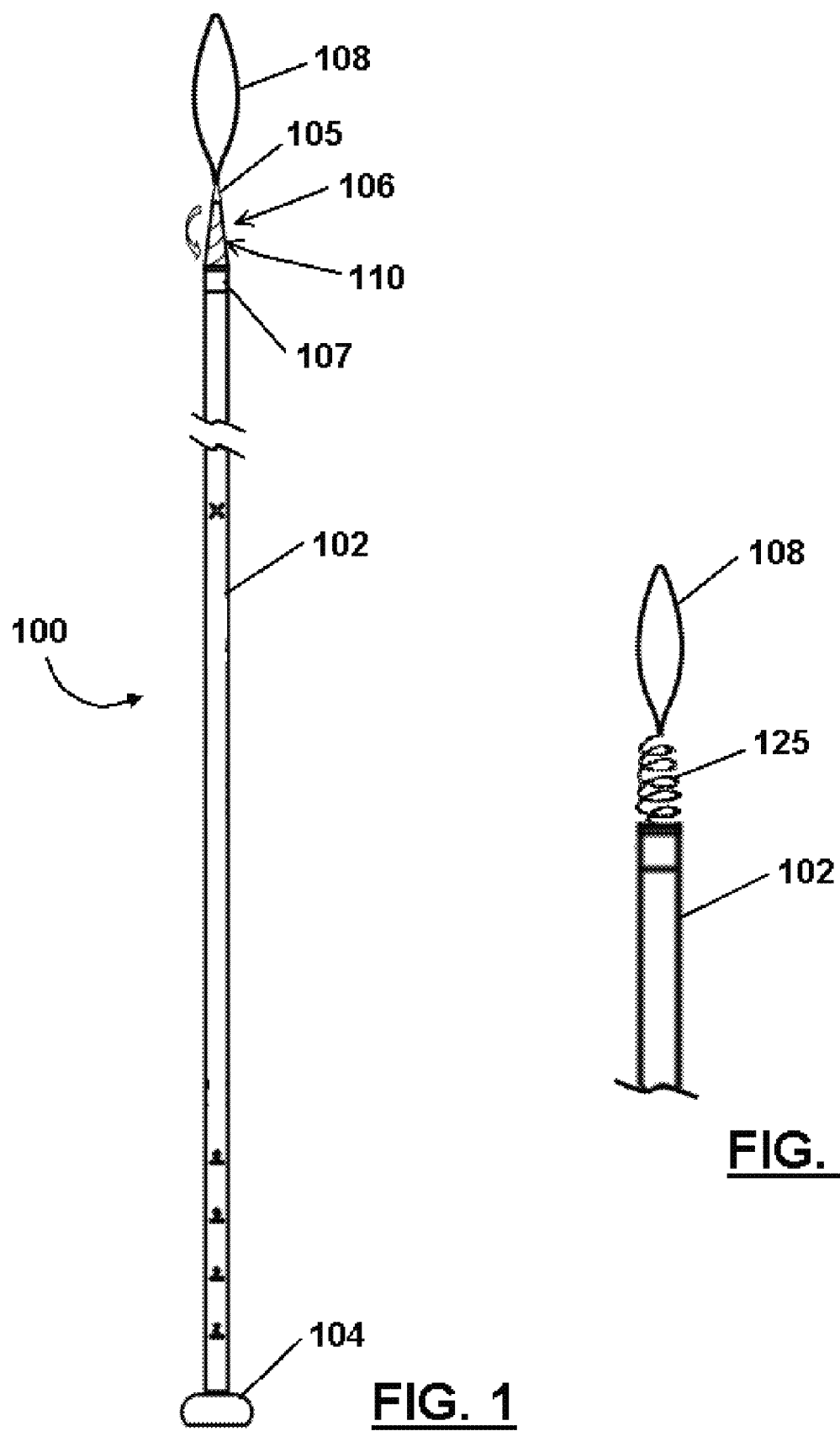

INTRODUCER FOR PERCUTANEOUS ENDOSCOPIC GASTROSTOMY APPLIANCE

CROSS-REFERENCE TO RELATED APPLICATIONS

This application is a non-provisional application which claims priority to U.S. provisional application Ser. No. 61/738,608, filed Dec. 18, 2012, which is incorporated by reference herein in its entirety.

TECHNICAL FIELD

Embodiments disclosed herein generally relate to medical devices. More particularly the present disclosure relates to a system and method for introducing a percutaneous endoscopic gastrostomy appliance.

BACKGROUND

Patients for whom normal ingestion of food becomes difficult or impossible may require placement of a feeding tube to assist in providing their nutritional needs. For some individuals, such as comatose patients, stroke victims, or those with a compromised gastrointestinal tract, this may require introduction of a feeding tube for delivery of nutritional products directly into the stomach or the jejunum. Tubes for delivery of nutritional products into the stomach are generally referred to as gastrostomy tubes, or "G"-tubes. Tubes for delivery of nutritional products into the jejunum are generally referred to as jejunostomy tubes, or "J"-tubes. In many cases in which a J-tube is utilized, the J-tube is inserted through the interior of a previously positioned G-tube.

There are two general methods for percutaneously positioning a gastrostomy tube in a patient, a procedure generally known as a Percutaneous Endoscopic Gastrostomy (PEG). One such method, referred to as the Ponsky ("pull") method involves introduction of an endoscope through the patient's mouth and esophagus and into the stomach. The endoscope contains a light source having sufficient power such that the position of the endoscope can be visualized on the outside of the patient's abdomen. An incision is made through the abdominal wall, then a trocar needle is passed therethrough into the stomach and is visualized by the endoscope. The needle is removed, leaving the trocar. A looped wire is passed through the trocar and is grasped/captured by a snare/forceps (usually disposed through a working channel of the endoscope). The endoscope, snare/forceps, and wire are pulled up through the esophagus and out through the mouth. The wire is then fastened with a knot or other means to the end of the gastrostomy tube, which often includes a dilator portion having a leading lower-diameter portion that expands to the full gastrostomy tube diameter along its length. This assembly is then pulled back down through the esophagus and stomach. The leading end of the wire and the external portion of the gastrostomy tube are pulled out through the aperture in the abdominal wall initially formed by the trocar needle. Typically, an internal bolster, such as a balloon, is provided internal of the stomach to hold the stomach against the abdominal wall, and an external bolster is provided external of the abdomen for anchoring the device exterior of the patient's skin.

The other method is commonly referred to as the "push" method. In this method, the endoscope is used to provide the physician with visualization of the stomach. An incision is made through the abdominal wall, then a trocar needle is passed therethrough into the stomach and is visualized by the endoscope. The needle is removed, leaving the trocar. A wire guide is passed through the trocar and is grasped/captured by a snare/forceps (usually disposed through a working channel of the endoscope). The endoscope, snare/forceps, and wire are pulled up through the esophagus and out through the mouth. the gastronomy tube (commonly with a leading dilator) is threaded over the wire guide. Then, the gastronomy tube assembly is advanced ("pushed") over the wire through the mouth, esophagus, and stomach to the incision. When it is visible through the incision, the assembly is pulled until its internal bolster contacts the interior wall of the stomach. Following placement via either of these two methods, proper positioning of the internal bolster against the stomach wall may be confirmed with the endoscope. Further background on relevant techniques may be understood with reference to PCT Pat. Publ. No. WO2010/075032 to Farrell et al., which is incorporated herein by reference.

In both procedures, the process of directing the dilator and/or gastrostomy tube through the abdominal wall can cause "tenting." "Tenting" is the distortion of body wall tissue being pushed/pulled away from the patient's body core as it frictionally contacts the outer circumference of the dilator and/or gastrostomy tube being directed therethrough. Many physicians would prefer to avoid this tissue distortion.

It may be desirable to provide to provide a dilator and/or gastrostomy tube that minimizes tissue displacement during introduction of the gastrostomy tube and that—by minimizing or preventing tenting—will improve physician's perception and performance of the procedure.

BRIEF SUMMARY

In one aspect, embodiments of a percutaneous gastrostomy introduction system disclosed herein may include may include an elongate tube assembly including one or both of a dilator portion and a gastrostomy tube portion, which may be continuously formed or joined by a connection that may—in certain embodiments—provide for rotation about a common longitudinal axis. The dilator portion may be generally conically tapered and be disposed near (including up to and defining) a first end of the elongate tube assembly. An engagement structure, including—for example—one or more of a wire loop, a user-graspable handle, or another graspable structure may be included at the first end of the device. A second end, opposite the first end, may include a bolster or other structure having a larger outer diameter than that of the gastrostomy tube portion. The dilator (if present) or other first end length of the elongate tube body may include at least one threaded external surface near the first end that, when contacting another surface, promotes rotation around a longitudinal axis generally defined by the tube assembly and that longitudinally advances the elongate tube by said contact.

In one aspect, embodiments disclosed herein may also include methods for introducing the device through a patient's body wall. In certain embodiments, an introducer accessory, which may be constructed as an external bolster, may be provided with a central aperture that engages the threaded external tube surface for advancement through the patient body wall. In certain preferred embodiments, the introducer accessory contacts a patient body wall sufficiently to prevent tenting during passage therethrough of the tubular body.

BRIEF DESCRIPTION OF THE DRAWINGS

FIG. 1 shows one embodiment of a percutaneous gastrostomy introduction system;

FIG. 1A shows a detail view of one portion of a variant embodiment of a percutaneous gastrostomy introduction system, while

DETAILED DESCRIPTION

Figure 1B:
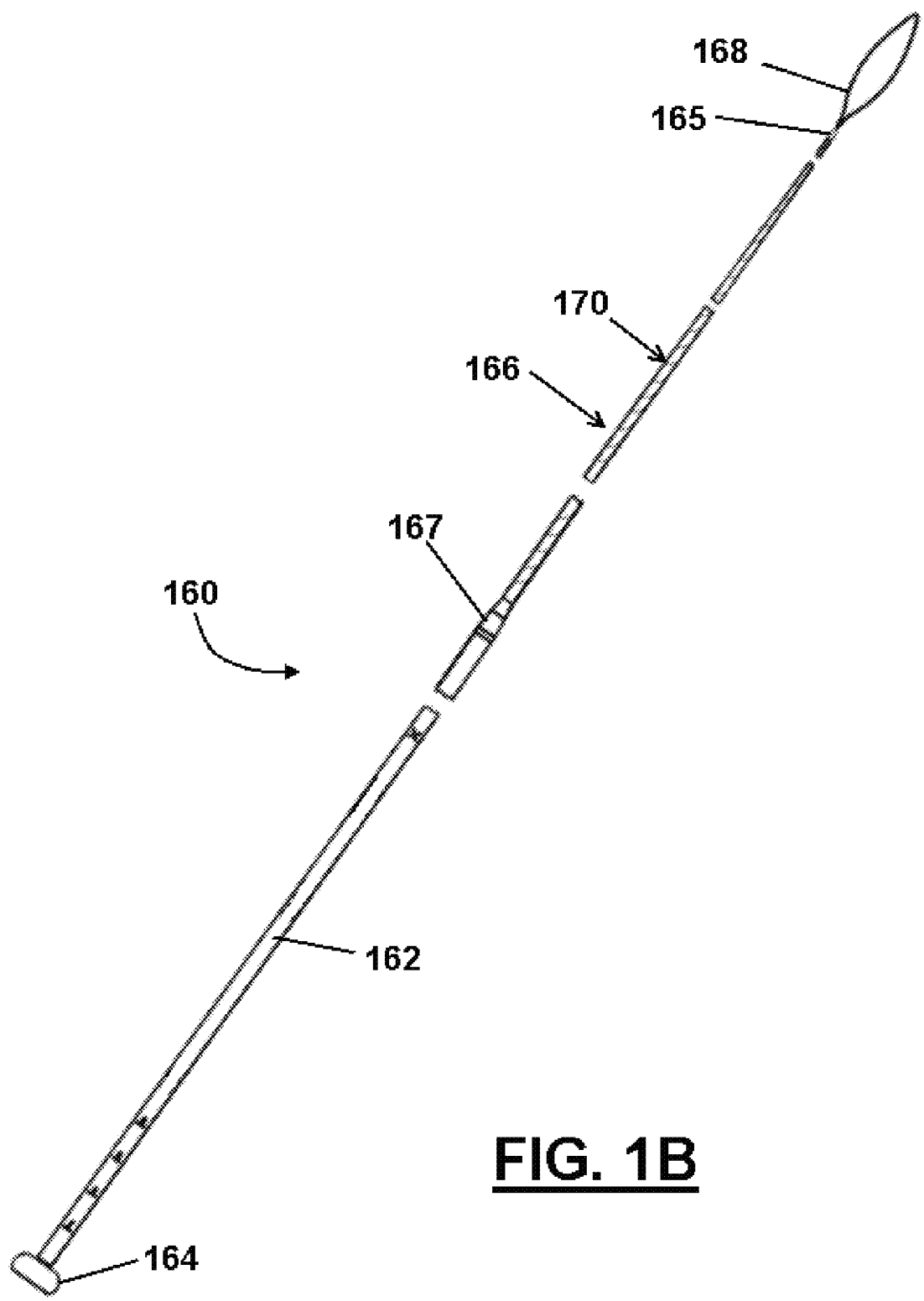
FIG. 1B shows a view of an entire system embodiment using intermediate truncations to account for length.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example— conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. The terms "proximal" and "distal" are used herein in the common usage sense where they refer respectively to a handle/doctor-end of a device or related object and a tool/patient-end of a device or related object.

One embodiment of a percutaneous endoscopic gastrostomy introduction system 100 is described with reference to FIG. 1, which shows an elongate tube assembly including a gastronomy tube portion 102 with a rounded end structure 104, a conically-tapered dilator portion 106, and an engagement structure embodied as a wire loop 108. Those of skill in the art will appreciate that the illustrated structure forms a central longitudinal axis common to the tube portion 102 and the dilator portion 106.

The transitions (i) between the tube portion 102 and the dilator portion 106 and (ii) between the dilator portion 106 and engagement structure 108 each may include a rotary joint 105, 107. The rotary joint(s) 105, 107, when present, will provide relative rotation between adjacent components around the longitudinal axis. Those of skill in the mechanical arts will appreciate that appropriate rotary joints may be constructed in a variety of manners including sealed or unsealed bearing joints, peg/loop joints, captive ball-socket joints, or other constructions.

The tapered outer surface of the dilator portion 106 of the elongate tube includes at least one helically-threaded surface 110 around its outer circumference. The helically-threaded surface 110, when contacting another surface, promotes rotation around the longitudinal axis and thereby longitudinally advances the elongate tube by said contact. Those of skill in the mechanical arts will appreciate, with reference to FIG. 1, that when a user pulls the wire loop 108 through a small opening (e.g., a small incision in a patient's body wall) contacting the outer circumference of the dilator portion 106, the contact between the threaded surface of the dilator 106 and the boundary of the opening will rotate the dilator 106 around its central longitudinal axis and radially disperse the forces in a manner that will effectively decrease or prevent tenting around the opening when the opening is through a pliable material.

The embodiment 100 of FIG. 1 may be considered a "short taper" embodiment, where the dilator portion 106 is relatively short in length relative to the overall device length. In certain embodiments, the short-taper dilator may be less than about 3 cm in length and equal to or less than about 5% of the total device length.

FIG. 1A illustrates a first end detail of an embodiment without a conical dilator between the tube portion 102 and the engagement structure 108. Instead, this embodiment includes a helically-spiraled introducer length 125, the helical outer surface of which will function similarly to the conical threaded dilator surface, promoting rotation and minimizing direct linear force/friction between the outer circumference of that portion and the inward-facing surface of an opening through which it is being drawn (e.g., parallel with the longitudinal axis). The outer diameter of the spiral 125 may taper, may be generally consistent, or may otherwise vary. The engagement structure 108 may be attached (as shown) to the helically-spiraled introducer length 125, or it may be connected (e.g., by one or more wires or other structures extending through the central lumen defined by the helically-spiraled introducer length 125) to the tube length 102.

Another embodiment of a percutaneous endoscopic gastrostomy introduction system 160 is described with reference to FIG. 1B, which shows an elongate tube assembly including a gastronomy tube portion 162 with a rounded end structure 164, an elongate conically-tapered dilator portion 166, and an engagement structure embodied as a wire loop 168. Those of skill in the art will appreciate that the illustrated structure forms a central longitudinal axis common to the tube portion 162 and the dilator portion 166.

The transitions (i) between the tube portion 162 and the dilator portion 166 and (ii) between the dilator portion 166 and engagement structure 168 each may include a rotary joint 165, 167. The rotary joint(s) 165, 167, when present, will provide relative rotation between adjacent components around the longitudinal axis. Those of skill in the mechanical arts will appreciate that appropriate rotary joints may be constructed in a variety of manners including sealed or unsealed bearing joints, peg/loop joints, captive ball-socket joints, or other constructions. As with the embodiment of FIG. 1, one or the other of the joints 165, 167 may be fixed.

The tapered outer surface of the dilator portion 166 of the elongate tube includes at least one helically-threaded surface 170 around its outer circumference. The helically-threaded surface 170, when contacting another surface, promotes rotation around the longitudinal axis and thereby longitudinally advances the elongate tube by said contact. Those of skill in the mechanical arts will appreciate, with reference to FIG. 1B, that when a user pulls the wire loop 168 through a small opening (e.g., a small incision in a patient's body wall) contacting the outer circumference of the dilator portion 166, the contact between the threaded surface of the dilator 166 and the boundary of the opening will rotate the dilator 166 around its central longitudinal axis and radially disperse the forces in a manner that will effectively decrease or prevent tenting around the opening when the opening is through a pliable material. The same will be true if/when the tube device 160 is being pushed through the opening.

The embodiment 160 of FIG. 1B may be considered a "long-taper" embodiment, where the dilator portion 166 is longer relative to the overall device length. In certain embodiments, the long-taper dilator may be greater than about 3 cm in length and/or greater than about 5% of the total device length. This long-taper construction may provide additional assistance in preventing tenting as the dilator portion 166 is passed through a patient's body wall, as the degree of tapering will be more gradual relative to the longitudinal axis, which is the axis of passage through the body wall opening.

Figure 2:
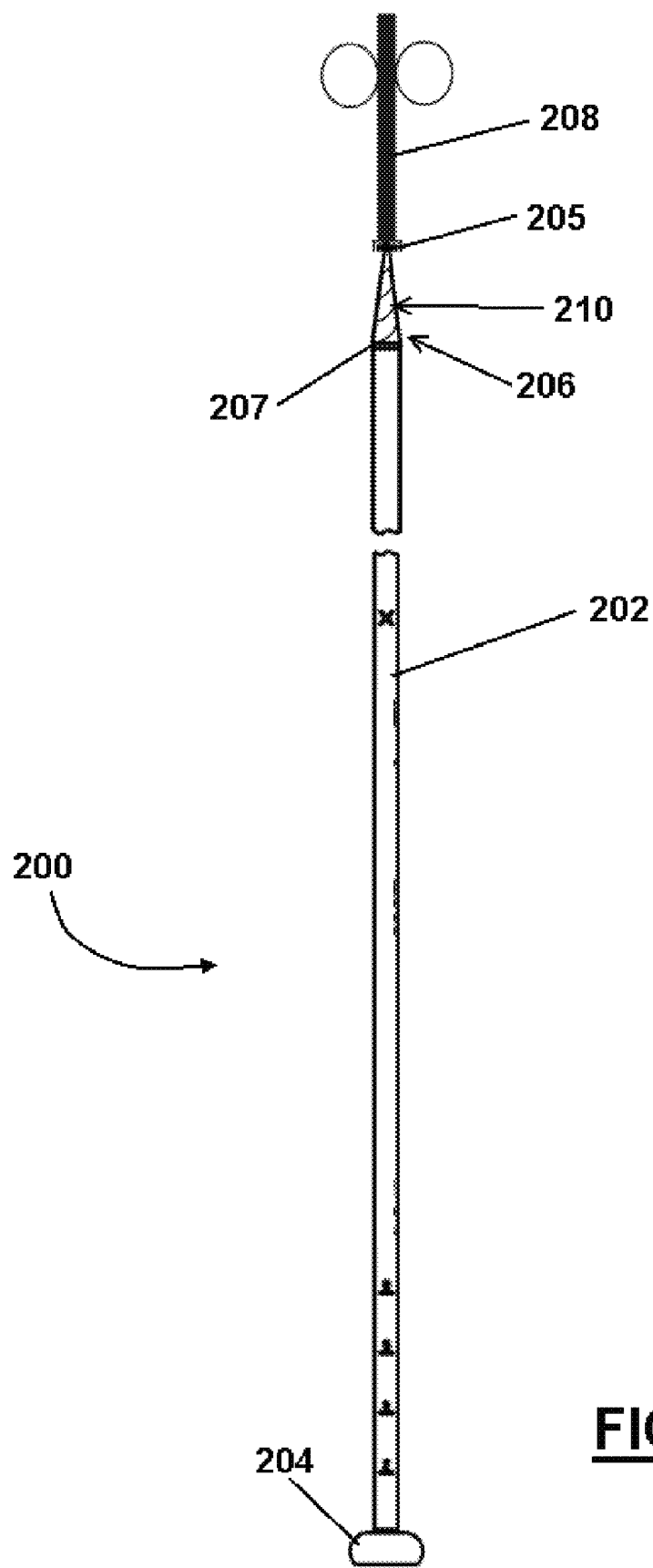
FIG. 2 shows another embodiment of a percutaneous gastrostomy introduction system.

Another embodiment of a percutaneous endoscopic gastrostomy introduction system 200 is described with reference to FIG. 2, which shows an elongate tube assembly including a gastronomy tube portion 202 with a rounded end structure 204, a conically-tapered dilator portion 206, and an engagement structure embodied as a user-graspable handle 208. Those of skill in the art will appreciate that the illustrated structure forms a central longitudinal axis common to the tube portion 202 and the dilator portion 206.

The transitions (i) between the tube portion 202 and the dilator portion 206 and (ii) between the dilator portion 206 and engagement structure 208 each may include a joint 205, 207. As with the other embodiments illustrated above, one or both joints may be fixed or rotary. The rotary joint(s), when present, provide relative rotation between adjacent components around the longitudinal axis. Those of skill in the mechanical arts will appreciate that appropriate rotary joints may be constructed in a variety of manners including sealed or unsealed bearing joints, peg/loop joints, captive ball-socket joints, or other constructions. In this embodiment, the first-end joint 205 is fixed, which allows a user to rotate the handle 208 while exerting a desired amount of first-end directed force along the longitudinal axis. In embodiments where the second-end joint 207 is also fixed, the entire device may rotate around its longitudinal axis, and in embodiments where the second-end joint 207 is rotary, only the dilator portion 206 will rotate with the handle 208.

The tapered outer surface of the dilator portion 206 of the elongate tube includes at least one helically-threaded surface 210 around its outer circumference. The helically-threaded surface 210, when contacting another surface, promotes rotation around the longitudinal axis and thereby longitudinally advances the elongate tube by said contact. Those of skill in the mechanical arts will appreciate, with reference to FIG. 2, that when a user engages the handle 208 with the first-end joint 205 to move the device through a small opening (e.g., a small incision in a patient's body wall) contacting the outer circumference of the dilator portion 206, the contact between the threaded surface of the dilator 206 and the boundary of the opening will cooperate with rotating the dilator 206 around its central longitudinal axis and radially disperse the forces in a manner that will effectively decrease or prevent tenting around the opening when the opening is through a pliable material (such as, for example, the flesh of a patient's body wall). The handle 208 may be attachable/detachable from and/or over a loop of the type shown in FIGS. 1-1A, and it may be attached to such a loop after that loop is passed through an opening to assist with drawing a further length of the device through the opening.

Figure 3:
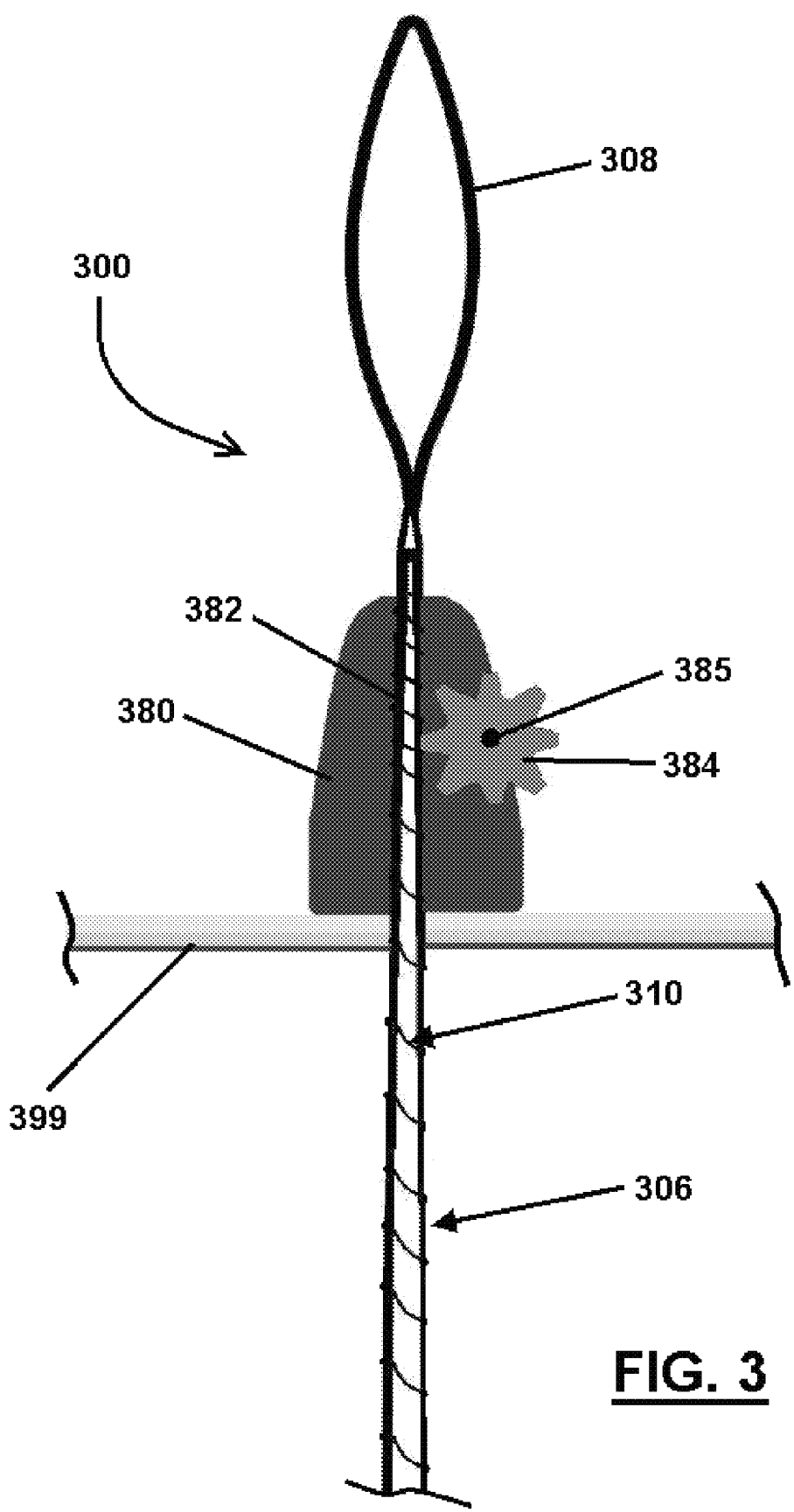
FIG. 3 shows yet another embodiment of a percutaneous gastrostomy introduction system.

FIG. 3 depicts the first end of another embodiment of a percutaneous endoscopic gastrostomy introduction system 300, and the method of deployment for each of the embodiments disclosed herein will be understood by those of skill in the art with reference to FIG. 3 (regarding the environment, although other embodiments may not include the accessory shown in FIG. 3). The system 300 is shown with the dilator 306 passed through a small opening transecting a patient's body wall 399 (illustrated only diagrammatically without differentiating the layers of the body wall and the wall of the stomach or intestine, which those of skill in the art will appreciate are implicated in methods using the presently-disclosed embodiments. The system may be a short-taper or a long taper system and is shown to include a conically-tapered dilator portion 306, an engagement structure embodied as a wire loop 308, and an introducer accessory 380. The tapered outer surface of the dilator portion 306 of the elongate tube includes at least one helically-threaded surface 310 around its outer circumference. The helically-threaded surface 310, when contacting another surface, promotes rotation around the longitudinal axis and thereby longitudinally advances the elongate tube by said contact.

In this embodiment, a portion of the contact is provided by a central longitudinal aperture 382 through the accessory 380, which is shown in longitudinal section view. The accessory 380 includes at least one toothed gear 384 rotatably mounted to the introducer accessory and including teeth configured to engage the at least one threaded surface 310 of the elongate tube assembly. The engagement of the at least one rotatably mounted toothed gear 384 including teeth with the at least one threaded surface 310 of the dilator length rotates the first end of the tube assembly about its longitudinal axis and moves it longitudinally relative to the at least one element. The toothed gear 384 (which may be embodied as a plurality of toothed gears) is disposed in and rotates in a plane congruent with the elongate tube's longitudinal axis. The rotational axis 385 of the toothed gear(s) is transverse to said plane and to said longitudinal axis. Those of skill in the art will appreciate that a toothed (including an internally-threaded) gear could be constructed coaxially around the aperture 382 to engage the dilator threads, or the gear could be constructed as a worm gear with a rotational axis generally parallel to the common longitudinal axis of the dilator and the aperture.

An inner diameter of the aperture 382 sufficiently nearly approximates an outer diameter of the elongate tube assembly sufficiently to effectively prevent tenting of patient tissue when the elongate tube is disposed tightly through said tissue and a lower-end surface of the introducer accessory contacts said tissue. Those of skill in the mechanical arts will appreciate, with reference to FIG. 3, that a user may engage the dilator portion 306 through the aperture 382 to move the dilator portion 306 through a small opening (e.g., a small incision in a patient's body wall). The operative contact between the threaded surface of the dilator 306 and the toothed gear 384 (when rotated as shown extending into the inner diameter of the accessory aperture 382) will rotate the dilator 306 around its central longitudinal axis and radially disperse the forces (at the contact surface between dilator and opening boundary) in a manner that will effectively decrease or prevent tenting around the opening when the opening is through a pliable material (such as, for example, the flesh of a patient's body wall). This tenting-prevention functionality may be assisted by the contact of the accessory the surface surrounding the opening.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A percutaneous endoscopic gastrostomy introduction system, comprising:
    an elongate tube assembly including a dilator portion, a gastrostomy tube portion, or both;
    a first end of the tube assembly, where the dilator portion—if present—is nearer the first end than the gastrostomy tube portion;
    a second end of the tube assembly longitudinally distant from the first end;
    an engagement structure disposed upon the first end; and
    at least one threaded external surface near the first end that, when contacting another surface, promotes rotation around a longitudinal axis generally defined by the tube assembly and longitudinally advances the elongate tube by said contact.

2. The system of claim 1, further comprising at least one rotary joint between the first end and the second end, the rotary joint configured to allow rotation of the first end relative to the second end, around the longitudinal axis.

3. The system of claim 2, where the at least one rotary joint comprises at least two rotary joints.

4. The system of claim 2, where both dilator and gastrostomy tube portions are present and where the at least one rotary joint is disposed therebetween in a manner allowing the dilator to rotate relative to the gastrostomy tube and vice versa.

5. The system of claim 1, further comprising an introducer accessory that includes an aperture, where the aperture accommodates passage therethrough of at least a portion of the elongate tube assembly, where at least one element of the introducer accessory contacts the at least one threaded surface of the elongate tube assembly, and where the contact promotes the rotation around a longitudinal axis generally defined by the tube assembly.

6. The system of claim 5, where the at least one element of the introducer accessory comprises at least one toothed gear rotatably mounted to the introducer accessory and including teeth configured to engage the at least one threaded surface of the elongate tube assembly, where the engagement of the at least one rotatably mounted toothed gear including teeth with the at least one threaded surface of the elongate tube assembly rotates the first end of the tube assembly about its longitudinal axis and moves it longitudinally relative to the at least one element.

7. The system of claim 6, where the at least one toothed gear is disposed in and rotates in a plane congruent with the elongate tube's longitudinal axis, and where the rotational axis of the at least one toothed gear is transverse to said plane and to said longitudinal axis.

8. The system of claim 6, where an inner diameter of the aperture sufficiently nearly approximates an outer diameter of the elongate tube assembly sufficiently to effectively prevent tenting of patient tissue when the elongate tube is disposed tightly through said tissue and a lower-end surface of the introducer accessory contacts said tissue.

9. The system of claim 1, where the threaded surface comprises a tapering length with a smaller outer diameter nearer the first end and a larger outer diameter nearer the second end.

10. The system of claim 1, where the engagement structure comprises one of a wire loop, a rotating accessory that rotates relative to the threaded surface, a non-rotating accessory that does not rotate relative to the threaded surface, and any combination thereof.

11. The system of claim 10, comprising the non-rotating accessory that does not rotate relative to the threaded surface, where the threaded surface is also non-rotary relative to a non-threaded surface nearer the second end.

12. The system of claim 10, where the engagement structure comprises a handle graspable by a user and configured for the user to grip the handle generally transverse to the tube assembly's longitudinal axis and to pull the tube assembly lengthwise along said axis.

13. A method of placing a percutaneous endoscopic gastrostomy tube, the method comprising steps of:
    providing a system according to claim 1,
    directing the at least one threaded surface into circumferential contact with an opening in a patient's tissue; and
    advancing the tube through the opening in a manner where contact of the at least one threaded surface with the tissue causes the at least one threaded surface to rotate within and relative to the opening.

14. A method of placing a percutaneous endoscopic gastrostomy tube, the method comprising steps of:
    providing a system according to claim 7;
    aligning the introducer accessory aperture with an opening in a patient's tissue so that the introducer accessory contacts the tissue around the opening;
    directing the at least one threaded surface through the opening in a patient's tissue into the aperture;
    engaging the toothed gear with the at least one threaded surface; and
    advancing the tube through the opening by rotating the toothed gear in a manner where contact of the at least one threaded surface with the gear causes the at least one threaded surface to rotate within and to move longitudinally through to the opening.

15. The method of claim 14, further comprising maintaining contact between the introducer accessory and the patient tissue sufficient to effectively prevent tenting of the tissue around the opening therethrough.

16. A percutaneous endoscopic gastrostomy introduction system, comprising:
    an elongate tube assembly including a dilator portion continuous with a gastrostomy tube portion;
    where the dilator portion is disposed at a first end of the tube assembly, with a first end terminus having a smaller diameter that tapers generally conically outward to a larger diameter where the dilator portion meets the gastrostomy tube portion;
    a second end of the tube assembly longitudinally distant from the first end and defining a second end terminus of the gastrostomy tube portion;
    the dilator portion including an externally threaded surface such that contacting another surface promotes rotation around a longitudinal axis generally defined by the tube assembly.

17. The system of claim 16, further comprising at least one rotary joint between the dilator portion and the gastrostomy tube portion that allows the portions to rotate relative to each other around the longitudinal axis.

18. The system of claim 16, further comprising an introducer accessory that includes an aperture through which the elongate tube assembly is movably disposed, and that includes a toothed gear engagingly contacting the threaded surface, where the contact promotes the rotation around the longitudinal axis when the toothed gear is rotated about a central rotational axis of the gear, which axis is generally transverse to the longitudinal axis.

19. The system of claim 16, further comprising an engagement structure disposed upon the first end of the dilator portion, the engagement structure formed as a handle graspable by a user, as a wire loop, or as a combination thereof.

20. The system of claim 19, further comprising at least one rotary joint between the dilator portion and the engagement structure.

* * * * *